US 6,589,516 B1

(12) United States Patent
Eyre et al.

(10) Patent No.: US 6,589,516 B1
(45) Date of Patent: Jul. 8, 2003

(54) COMPOSITIONS CONTAINING BOSWELLIA EXTRACTS

(75) Inventors: Heather Eyre, Kent (GB); Maxine Jayne Hills, Kent (GB); Stephen David Watkins, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/913,952

(22) PCT Filed: Mar. 23, 2000

(86) PCT No.: PCT/GB00/01114

§ 371 (c)(1),
(2), (4) Date: Dec. 19, 2001

(87) PCT Pub. No.: WO00/57893

PCT Pub. Date: Oct. 5, 2000

(30) Foreign Application Priority Data

Mar. 26, 1999 (GB) .............................................. 9906914

(51) Int. Cl.⁷ ............................ A61K 7/06; A61K 35/78
(52) U.S. Cl. ...................... 424/70.1; 424/725; 424/401
(58) Field of Search ................................ 424/70.1, 401, 424/725

(56) References Cited

FOREIGN PATENT DOCUMENTS

EP          0 755 940       *  1/1997

OTHER PUBLICATIONS

Database DWPI, Derwent acc. No. 1999–369936, RD 422034, Use of Boswellia extracts, methyl pyrrolidone carboxylate, ceramides and pogamol—are useful in e.g. cosmetics, food stuffs and pharmaceuticals, Jun. 10, 1999, abstract.*

Database WPI, Section Ch, Week 199931, Derwent Publications Ltd., London, GB; Class A96, AN 1999–369936, XP00214933 Quest Int UK Ltd: "Use of Boswellia extracts, menthyl pyrrolidone carboxylate, ceramides and pongamol—are useful in e.g. cosmetics, food stuffs and pharmaceuticals" abstract & Research Disclosure, vol. 422, No. 034, Jun. 10, 1999, Emsworth, GB.

* cited by examiner

*Primary Examiner*—James M. Spear
*Assistant Examiner*—Blessing Fubara
(74) *Attorney, Agent, or Firm*—Morgan, Lewis & Bockius LLP

(57) ABSTRACT

A composition suitable for use on the skin or hair comprising: a) at least one extract of a Boswellia plant or at least one boswellic acid; and b) a carrier selected from the group consisting of branched fatty alcohols containing 8 to 32 carbon atoms, branched fatty acids containing 8 to 32 carbon atoms, unsaturated fatty alcohols containing 12 to 24 carbon atoms, unsaturated fatty acids containing 12 to 24 carbon atoms and derivatives of said branched fatty alcohols, said branched fatty acids, said unsaturated fatty alcohols and said unsaturated fatty acids, or mixtures thereof.

20 Claims, No Drawings

COMPOSITIONS CONTAINING BOSWELLIA EXTRACTS

This application is the National Phase of International Application PCT/GB00/01114 filed Mar. 23, 2000 which designated the U.S. and that International Application was published under PCT Article 21(2) in English.

FIELD OF INVENTION

The invention relates to compositions comprising at least one Boswellia extract, or at least one boswellic acid or derivative thereof. The compositions are suitable for application to the skin or hair.

BACKGROUND OF INVENTION

It has long been known that extracts of the Boswellia family of plants including Boswellia Serrata can produce a soothing effect to irritated skin and that this activity is due to the terpenoid compounds grouped under the general name boswellic acids. The different boswellic acids share the same basic pentacyclic triterpene (steroid-like) structure but differ in their side groupings.

EP-A-755.940 relates to a novel fraction and a process for the isolation of said fraction comprising a mixture of specified boswellic acids from the gum resin of Boswellia Serrata. The fraction is stated to exhibit anti-inflammatory, anti-arthritic and antiulcerogenic activity.

Typical extracts of Boswellia plants are solids or powders with a wide melting range—normally above 80° C. To allow for easy incorporation into compositions which are suitable for use on the skin or hair, an extract of Boswellia, containing the boswellic acids, or boswellic acids or derivatives thereof themselves, need to be dissolved or dispersed in a suitable carrier. Although they can be dissolved in solvents such as methanol, ethyl acetate, acetone and the like, these solvents are not suitable for use in typical skin and hair care formulations because of their aggressive solvent action on the skin and hair, and/or because of their high volatility and/or strong odour.

Ingredients which are commonly used in skin care or hair care formulations, such as glycerine, sorbitol, mineral oil, cyclomethicone, dimethicone and petrolatum are not suitable solvents or carriers for Boswellia extracts or boswellic acids or derivatives thereof as they are either too polar or not sufficiently polar.

Alkalies can produce aqueous solutions of boswellic acids by forming the respective salts. However, prolonged skin or hair contact by alkaline products (e.g. with a pH greater than 8.5) is not recommended, especially for sensitive skin or scalp, or for damaged hair.

We have now surprisingly found that a specified group of fatty alcohols or fatty acids, or derivatives, or mixtures thereof, are suitable carriers for dissolving and/or dispersing at least one Boswellia extract, or at least one boswellic acid or derivative thereof. Further, the carrier aids the incorporation of the extract, or acid, into compositions suitable for use on the skin or hair and improves the stability of said compositions containing the extract, or acid.

SUMMARY OF THE INVENTION

According to a first aspect of the invention, there is provided a composition suitable for use on the skin or hair comprising;
 a) at least one extract of a Boswellia plant, or at least one boswellic acid or derivative thereof; and
 b) a carrier selected from the group consisting of branched fatty alcohols containing 8 to 32 carbon atoms, branched fatty acids containing 8 to 32 carbon atoms, unsaturated fatty alcohols containing 12 to 24 carbon atoms, unsaturated fatty acids containing 12 to 24 carbon atoms, and derivatives of said branched fatty alcohols, said branched fatty acids, said unsaturated fatty alcohols and said unsaturated fatty acids, or mixtures thereof.

According to a second aspect of the present invention, there is provided a method of preparing a composition suitable for application to the skin or hair comprising mixing a composition comprising;
 a) at least one extract of a Boswellia plant, or at least one boswellic acid or derivative thereof; and
 b) a carrier selected from the group consisting of branched fatty alcohols containing 8 to 32 carbon atoms, branched fatty acids containing 8 to 32 carbon atoms, unsaturated fatty alcohols containing 12 to 24 carbon atoms, unsaturated fatty acids containing 12 to 24 carbon atoms, and derivatives of said branched fatty alcohols, said branched fatty acids, said unsaturated fatty alcohols and said unsaturated fatty acids, or mixtures thereof
with at least one cosmetically or pharmaceutically acceptable ingredient.

According to a third aspect of the present invention, there is provided a use of a composition comprising;
 a) at least one extract of a Boswellia plant, or at least one boswellic acid or derivative thereof; and
 b) a carrier selected from the group consisting of branched fatty alcohols containing 8 to 32 carbon atoms, branched fatty acids containing 8 to 32 carbon atoms, unsaturated fatty alcohols containing 12 to 24 carbon atoms, unsaturated fatty acids containing 12 to 24 carbon atoms, and derivatives of said branched fatty alcohols, said branched fatty acids, said unsaturated fatty alcohols and said unsaturated fatty acids, or mixtures thereof,
for preparing compositions suitable for application to the skin or hair.

The compositions of the invention comprise at least one extract of a Boswellia plant, or at least one boswellic acid or derivative thereof.

The compositions of the present invention suitably comprise a safe and effective amount, preferably from 0.005% to 50% by weight of the composition and more preferably from 0.05% to 25% by weight of the composition of at least one Boswellia extract, or at least one boswellic acid or derivative thereof.

Suitable extracts for use herein may be derived from the following Boswellia plants including Boswellia Cartenii, Boswellia Frereana, Boswellia Bhau-dajaina, Boswellia Serrata and Boswellia Thurifera. The preferred plants from which extracts are derived are Boswellia Serrata.

The extracts derived from Boswellia plants can comprise gums, oleo-gums, resins, essential oils and residues, or mixtures thereof. Preferred extracts for use herein are gums.

The Boswellia gum extract useful herein comprises a mixture of active triterpenoid compounds more commonly known as boswellic acids. All boswellic acids have a pentacyclic structure based on 12-ursen-24-oic acid with differing substituents. Many individual boswellic acid compounds have been isolated from the Boswellia extract including α- and β-boswellic acids and derivatives thereof. Of these, β-boswellic acid and derivatives thereof are thought to be the active components.

A typical extract comprising Boswellia Serrata gum resin will comprise greater than 50% by weight boswellic acids and often more than 60% by weight boswellic acids.

A typical extract of a Boswellia plant suitable for use herein comprises a mixture of boswellic acids comprising at least one of 3a-hydroxyurs-12-ene-24-oic acid, 3a-acetoxyurs-12-ene-24-oic acid, 3a-hydroxyurs-12-ene-11-keto-24-oic acid and 3a-hydroxyurs-9,12-dien-24-oic acid.

Boswellia extracts suitable for use herein are commercially available for example from Quest International, Kent, UK.

The compositions of the invention also comprise a carrier for the at least one extract of a Boswellia plant, or the at least one boswellic acid or derivative thereof.

In accordance with the invention, suitable carriers for this purpose are selected from the group consisting of branched fatty alcohols containing 8 to 32 carbon atoms, branched fatty acids containing 8 to 32 carbon atoms, unsaturated fatty alcohols containing 12 to 24 carbon atoms, unsaturated fatty acids containing 12 to 24 carbon atoms, and derivatives of said branched fatty alcohols, said branched fatty acids, said unsaturated fatty alcohols and said unsaturated fatty acids, or mixtures thereof.

The compositions of the present invention typically comprise from 50% to 99.995%, preferably from 75% to 99.95%, and even more preferably from 80% to 95% of a carrier by weight of the composition.

The preferred carriers for use herein are selected from branched fatty alcohols or branched fatty acids containing 8 to 32 carbon atoms, or mixtures thereof, which are liquids at room temperature. Preferably, the branched fatty alcohols and fatty acids are saturated. Saturated compounds generally have good stability against oxidation. More preferred, are saturated, branched fatty alcohols or fatty acids containing from 8 to 20 carbon atoms. Particularly useful branched fatty alcohols and fatty acids herein include isostearyl alcohol, isostearic acid, isocetyl alcohol, isopalmitic acid, octyldodecanol, octyldecanol, hexyldecanol, butyloctanol and ethylhexanol.

Unsaturated fatty alcohols and unsaturated fatty acids, containing 12 to 24 carbon atoms which are liquid at room temperature are also good carriers for Boswellia extracts. However, their presence may be disadvantageous in compositions requiring long term storage because as they are unsaturated, they have the potential to become oxidised and rancid over time. Preferred for use herein are unsaturated fatty alcohols or unsaturated fatty acids containing from 16 to 20 carbon atoms. Particularly useful unsaturated alcohols and unsaturated acids herein include oleyl alcohol, oleic acid, linoleic acid and linolenic acid.

Derivatives of the above described branched, or unsaturated fatty acids and alcohols are also good carriers for the Boswellia extract. Useful derivatives include the following:

(a) Ethoxylated derivatives that are liquid at room temperature. Useful ethoxylated derivatives herein include derivatives of branched fatty alcohols or acids and derivatives of unsaturated fatty alcohols or acids. Preferably, the number of ethylene oxide units per mole of fatty acid or fatty alcohol is in the range 1 to 15 and more preferably is in the range 1 to 10. It is also preferred that the derivative has a calculated HLB (hydrophilic/lipophilic balance) of less than 15 and preferably in the range 2 to 9.

(b) Esters of the abovementioned branched, or unsaturated fatty acids, the esters being liquid at room temperature. The fatty acids may be esterified with a wide variety of alcohols, including branched or linear, saturated or unsaturated alcohols. Preferably, the fatty acid is esterified with an alcohol containing from 2 to 18 carbon atoms. Preferred esters for use herein are branched or unsaturated fatty acids esterified with a hexitol anhydride. The esters of hexitol anhydrides can be mono-, di- or tri-esters but are preferably mono-esters (i.e. the ratio of acid to hexitol anhydride is 1:1). A particularly preferred hexitol anhydride from which to prepare an ester is sorbitan. Other preferred esters are monoesters of glycerol and a branched fatty acid (monoglycerides of branched fatty acids). Monoglyceride compositions herein contain at least 80 per cent by weight of a monoglyceride of a single acid. Yet other preferred esters are monoesters of propylene glycol, butylene glycol, hexylene glycol or dipropylene glycol and a branched or an unsaturated fatty acid.

(c) Esters of the branched fatty alcohols or unsaturated fatty alcohols, the esters being liquid at room temperature. The fatty alcohols may be reacted with a wide variety of acids, including branched or linear saturated or unsaturated acids and hydroxy acids such as ($\alpha$-hydroxy acids or $\beta$-hydroxy acids. Preferably, the acid contains from 2 to 18 carbon atoms.

(d) Ethoxylated derivatives of hexitol anhydride esters as defined in (b) above. The degree of ethoxylation is preferably from 1 to 15 ethylene oxide, units per mole of hexitol anhydride ester and the ethoxylated ester is liquid at room temperature.

(e) Ethoxylated derivatives of monoglycerides as defined in (b) above. The degree of ethoxylation is preferably from 1 to 15 ethylene oxide units per mole of monoglyceride and the ethoxylated monoglyceride is liquid at room temperature.

Generally, the carriers used in the compositions of the invention are liquid at room temperature. However, it is not essential that the carrier should be completely free from solid matter. Since many available fatty alcohols and fatty acids comprise mixtures of alcohols or acids, certain isomers can be present as solid matter in the mixture. The presence of such solid matter is not detrimental to the use of a particular carrier, provided that the carrier is fluid at room temperature. For the purposes of assessing fluidity in relation to this invention a temperature of 23° C. is assumed for "room temperature".

The carriers used in the compositions of the invention are capable of dispersing or dissolving the Boswellia extracts or boswellic acids or derivatives thereof. It is not essential that the extract or acid be completely soluble in the carrier, provided that the mixture of extract or acid and carrier can be incorporated into skin care or hair care products to produce a stable composition.

The carrier of the present invention may also include other exicipients conventionally added to compositions suitable for application to the skin or hair such as, silicones, solvents such as water, emollients, or emulsifiers for example.

Optionally, the compositions herein may comprise conventional ingredients normally present in compositions for application to the skin or hair. Non-limiting examples of such ingredients include alkanolamide surfactants, alkyl polyglucose derivatives, alkyl ether sulphate surfactants, allantoin, aloe barbadensis mil (aloe vera linne), $\alpha$-hydroxycarboxylic acids, aluminium chlorhydrate and its derivatives, aluminium salts, amide derivatives, amino acids, amphoteric surfactants, ascorbic acid and its salts, bentonite and hectorite, benzyl alcohol, bisabolol, butane propellants, carboxy vinyl polymer water soluble salts, carboxy methylcellulose, carrageenan, cetrimonium salts, cholesterol, cocamidopropyl betaine, depilatories, dihydroxyacetone, dimethyl ether, ethanol, fatty acids, fatty acid citrate esters, fatty alcohols, fragrance ingredients, glucose esters of higher fatty acids, glycerin, glyceryl stearates, glycols, guar gum, gum arabic, hyaluronic acid, hydroxybenzoic acids, hydroquinone, isopropyl alcohol, kojic acid, lanolin, lauryl betaine, lipids extracted from the biomass of microorganisms, yeasts, moulds and bacteria, liposomes, liquorice (glycyrrhiza glabra) and its components (glycyrrhetinic acid, glycyrrhizic acid, etc.), low molecular weight acidic mucopolysaccharides & their salts, low molecular weight humectant components, magnesium aluminium silicate, methacrylate polymers, mineral oils, mineral powders, natural or synthetic amino acid with protein or peptide bond, natural moisturing factor ingredients eg lactic acid. non-volatile silicones, oil agent(s), oil matter, oligosaccharide(s), organic acids, pantothenic acid and its derivatives, petroleum jelly, phospholipid, polysaccharides eg locust bean gum, polyvinyl alcohol, polypeptides, proteins, piroctone olamine, quaternised silicone derivatives, raffinose, saponins, sodium chloride, sodium cocoyl isethionate, sodium hyaluronate, sources of linoleic acid, sterols, sterol esters, sucrose, sugar esters of higher fatty acids, sunscreens, surfactants, talc, tea tree oil (Melaleuca spp.), thioglycolic acid and its derivatives, titanium dioxide, tocopherol and esters thereof, triclosan, mono- or di- or triglycerides, vegetable oils, vitamins and analogues, volatile silicone fluids, water, water soluble moisture-retaining agents, water soluble polymers, waxes, zinc oxide, zinc pyrithione.

The compositions of the present invention may be used in a wide range of products suitable for use on, or application to, the skin or hair particularly, but not exclusively, cosmetic compositions. Such products may be formulated in various product forms such as lotions, creams, gels, sticks, solutions, aerosols, solid soaps or liquid cleansers. Thus, in a further aspect, the present invention provides a product for application to the skin or hair comprising a composition in accordance with the invention. The term skin as used herein, means any outer surface of the body including the nails.

When products comprising a composition in accordance with the invention are prepared, the composition of the invention can be separately prepared and added to the other ingredients of the desired product, or the compositions of the invention can be formed during the manufacture of the product.

The invention is illustrated by the following non-limiting examples.

EXAMPLE 1

Carrier/Boswellia Serrata Extract Blends

Compositions according to the invention were prepared by mixing ingredients in the amounts listed below.

| Composition 1) | Boswellia Serrata Gum Resin Extract | 10% w/w |
| | Isostearyl Alcohol | 90% w/w |
| Composition 2) | Boswellia Serrata Gum Resin Extract | 15% w/w |
| | Isostearic Acid | 85% w/w |
| Composition 3) | Boswellia Serrata Gum Resin Extract | 5% w/w |
| | Oleic Acid | 95% w/w |
| Composition 4) | Boswellia Serrata Gum Resin Extract | 15% w/w |
| | Polyoxyethylene (2) oleyl alcohol | 85% w/w |
| Composition 5) | Boswellia Serrata Gum Resin Extract | 5% w/w |
| | Polyoxyethylene (3) isostearic acid | 95% w/w |
| Composition 6) | Boswellia Serrata Gum Resin Extract | 10% w/w |
| | Sorbitan monolaurate | 90% w/w |
| Composition 7) | Boswellia Serrata Gum Resin Extract | 20% w/w |
| | Polyoxyethylene (20) sorbitan monolaurate | 80% w/w |
| Composition 8) | Boswellia Serrata Gum Resin Extract | 5% w/w |
| | Isopropyl isostearate | 95% w/w |

EXAMPLE 2

An Aftersun Cream Gelee was prepared according to the following formulation.

| INGREDIENT | INCI NAME | w/w % |
| --- | --- | --- |
| Phase A: | | |
| Deionised Water (A) | | to 100% |
| Klucel-99-H | Hydroxypropylcellulose | 0.20 |
| Carbopol ultrez 10 | Carbomer | 0.80 |
| Phase B: | | |
| Boswellia Serrata Gum Extract | Boswellia Serrata | 0.15 |
| Isostearyl alcohol | Isostearyl Alcohol | 1.35 |
| Euxyl K400 | Methyldibromoglutaronitrile and phenoxyethanol | 0.10 |
| Cremaphor RH 40 | PEG-40 hydro castor oil | 0.30 |
| Flamingo pearl blue 100 | | 0.50 |
| Phase C: | | |
| Netrol TE | Tetrahydroxypropyl ethylenediamine | 0.20 |
| Deionised Water | | 4.40 |
| Quest perfume | | 0.50 |

(Klucel-99-H, Carbopol, Euxyl K400, Cremaphor RH 40 and Netrol TE are all Trade Marks.)

Deionised water (A) and hydroxypropylcellulose were combined and mixed under very high shear for 1 hour. Carbomer was added and left to wet out. Phase B was prepared by combining the ingredients with heating to 65° C. and was then added to A with minimal shearing so as to avoid breaking down the structure. Phase C was prepared by combining the ingredients and added to the mixture of Phases A and B and the combined mixture was stirred gently for 15 minutes.

The presence of Boswellia Serrata extract helps to reduce redness and irritation and produces an even skin tone.

EXAMPLE 3

An Acne Mininising Night Cream was prepared to the following formulation.

| INGREDIENT | INCI NAME | w/w % |
| --- | --- | --- |
| Phase A: | | |
| Oleyl alcohol | | 4.00 |
| Crodamol OP | 2-Ethylhexyl palmitate | 8.00 |
| Dow Corning 200/350 | Dimethicone | 0.50 |
| Emcol E 607S | Steapyrium chloride | 3.50 |
| Dry Flo PC | Aluminium starch octenyl succinate | 4.00 |
| Boswellia Serrata Gum Extract | Boswellia Serrata | 0.50 |

-continued

| INGREDIENT | INCI NAME | w/w % |
|---|---|---|
| Phase B: | | |
| Deionised water | | to 100.00 |
| Lactic acid | | 2.50 |
| Sodium lactate | | 2.00 |
| Phase C: | | |
| Xanthan XP | Xanthan gum | 0.40 |
| Glycerin | | 1.50 |
| Phase D: | | |
| Euxyl K400 | Methyldibromoglutaronitrile and Phenoxyethanol | 0.10 |
| Quest perfume | | 0.50 |

(Crodamol OP, Dow Corning 200/300, Emcol E 6075, Dry Flo PC, Xanthan XP and Euxyl K400 are all Trade Marks.)

Phase B was prepared by combining the ingredients. Phase C was prepared by combining the ingredients and was added to Phase B using high shear. Phase A was prepared by combining the ingredients and this mixture and Phase A were heated to 75° C. Phase A was added to the mixture using shear, and then cooled with stirring to 40° C., when Phase D was added and stirred in thoroughly.

The Boswellia Serrata Extract produced calming benefits in this cream which are especially good for problematic and sensitive skin.

EXAMPLE 4

An After Hair Removal Cream was prepared according to the following formulation.

| INGREDIENT | INCI NAME | w/w % |
|---|---|---|
| Phase A: | | |
| Deionised water | | to 100.00 |
| Propylene glycol | | 1.80 |
| Dipropylene glycol | | 0.50 |
| Carbopol ultrez | Carbomer | 0.20 |
| Glycerine | | 0.25 |
| Sepigel 305 | Polyacrylamide, C13–14 isoparaffin | 0.30 |
| Lubrajel TW | Polyglycerylmethacrylate and Propylene glycol | 0.50 |
| Algisium C | Methylsilanol mannuronate | 0.20 |
| Phase B: | | |
| Finsolv TN | C12–C15 alkyl benzoate | 2.00 |
| Dow Corning 344 | Cyclomethicone | 4.50 |
| Polysynlane | Hydrogenated polyisobutene | 1.60 |
| Wickenol 153 | Isotridecyl isononanoate | 2.00 |
| Isostearyl alcohol | | 4.50 |
| Dow Corning 200/350 | Dimethicone | 0.20 |
| Questamide H | Bishydroxyethyl Biscetyl Malonamide | 0.80 |
| Boswellia Serrata Gum Extract | Boswellia Serrata | 0.10 |
| Myristic acid | | 0.40 |
| Cetearyl alcohol | | 4.00 |
| Ceraphyl 375 | Isostearyl neopentanoate | 0.50 |

-continued

| INGREDIENT | INCI NAME | w/w % |
|---|---|---|
| Phase C: | | |
| Triethanol amine | | 0.20 |
| Phenonip | Phenoxyethanol, methylparaben Ethylparaben, propylparaben, butylparaben | 0.50 |
| Apricot extract | | 0.30 |
| Quest perfume | | 0.50 |

(Carbopol, Sepigel 305, Lubragel TW, Algisium C, Finsolv TN, Dow Corning 344, Polysynlane, Wickenol 153, Dow Corning 200/300, Questamide H, Ceraphyl 375 and Phenonip are all Trade Marks.)

Phase A and Phase B were separately prepared by combining the ingredients and heated to 75° C. when Phase B was added to Phase A, and the triethanolamine was added. The emulsion was stirred until it was homogeneous and cooled. When the temperature reached 40° C., the preservative (Phenonip) and apricot extract and perfume were added and stirred in thoroughly.

Due to the calming benefits of the Boswellia extract this cream prevents the appearance of red dots which usually appear after shaving as well as waxing or other ways of removing hair.

EXAMPLE 5

A shampoo suitable for cleansing a baby's hair and scalp was prepared according to the following formulation:

| INGREDIENT | INCI NAME | w/w % |
|---|---|---|
| Phase A: | | |
| Deionised water | | to 100.00 |
| Tween 20 | Polysorbate 20 | 25.00 |
| Empicol TL40/T | TEA-Lauryl Sulfate | 20.00 |
| Plantacare 1200 | Decyl Polyglucose | 7.50 |
| Tego Betain F50 | Cocamidopropyl Betaine | 2.50 |
| Germaben-II | Diazolidinyl Urea & Methylparaben & Propylparaben & Propylene Glycol | 0.40 |
| Nervanaid BA2 | Disodium EDTA | 0.10 |
| Uvinul MS40 | Benzophenone-4 | 0.03 |
| Cetiol HE | PEG-7 Glyceryl Cocoate | 0.60 |
| Phase B: | | |
| Boswellia Serrata Gum Extract | Boswellia Serrata | 0.10 |
| Dipropylene Glycol | Dipropylene Glycol | 1.00 |
| Isostearic acid | Isostearic Acid | 0.50 |
| Perfume | | 0.50 |
| Sodium chloride | | 2.50 |

(Tween 20, Empicol TL40/T, Plantacare 1200, Tego Betain F50, Germaben-II, Nervanaid BA2, Uvinul MS40 and Cetiol HE are all Trade Marks.)

Phase A was prepared by firstly dissolving with stirring the disodium EDTA and benzophenone-4 in water. The remaining ingredients of Phase A were then combined with this solution, stirring the mixture between each addition.

Phase B was prepared by combining the ingredients with heating to 65° C. This mixture was then combined with Phase A. Perfume was then added to the mixture of Phases A and B and the combined mixture thickened upon the addition of sodium chloride.

The presence of Boswellia Serrata extract helps to calm and prevent irritation caused by surfactants.

EXAMPLE 6

A hair shampoo suitable for frequent use was prepared according to the following formulation:

| INGREDIENT | INCI NAME | w/w % |
|---|---|---|
| Phase A: | | |
| Deionised water | | to 100.00 |
| Empicol ESB3 | Sodium Laureth Sulfate (28%) | 20.00 |
| Texapon ALS | Ammonium Sulfate | 20.00 |
| Plantacare 818 | Coco Glucoside | 7.50 |
| Tego Betain F50 | Cocamidopropyl Betaine | 2.50 |
| Nervanaid BA2 | Disodium EDTA | 0.10 |
| Cetiol HE | PEG-7 Glyceryl Cocoate | 0.60 |
| Germaben-II | Diazolidinyl Urea & Methylparaben & Propylparaben & Propylene Glycol | 0.40 |
| Phase B: | | |
| Boswellia Serrata Gum Extract | Boswellia Serrata | 0.20 |
| Dipropylene Glycol | Dipropylene Glycol | 1.00 |
| Isostearic acid | Isostearic Acid | 0.40 |
| Propylene Glycol | Propylene Glycol | 0.60 |
| Perfume | | 0.50 |
| Sodium chloride | | 2.50 |

(Empicol ESB3, Texapon ALS, Plantacare 818, Tego Betain F50, Nervanaid BA2, Cetiol HE, and Germaben-II are all Trade Marks.)

Phase A was prepared by dissolving the disodium EDTA in water with stirring. The remaining ingredients of Phase A were then combined with this solution, stirring the mixture between each addition.

Phase B was prepared by combining the ingredients with heating to 65° C. This mixture was then combined with Phase A. Perfume was then added to the mixture of Phases A and B and the combined mixture thickened upon the addition of sodium chloride.

The presence of Boswellia Serrata extract helps to prevent and calm irritation caused by surfactants.

EXAMPLE 7

A depilatory cream was prepared according to the following formulation.

| INGREDIENT | INCI NAME | w/w % |
|---|---|---|
| Phase A: | | |
| Cetyl Alcohol | | 5.00 |
| Eumulgin B3 | Ceteareth-30 | 2.00 |
| Mineral Oil | | 7.00 |
| Boswellia Serrata Gum Extract | Boswellia Serrata | 0.20 |
| Isostearyl Alcohol | Isostearyl Alcohol | 1.80 |
| Phase B: | | |
| Water | | to 100.00 |
| Carbopol Ultrez | Carbomer | 1.50 |
| Dipropylene Glycol | | 2.00 |
| Potassium Thioglycolate (40%) | | 10.00 |
| Potassium Hydroxide | | 2.50 |

(Eumulgin B3 and Carbopol are Trade Marks.)

Phase B was prepared by combining the carbomer and dipropylene glycol with water and allowing the carbomer to wet out. Potassium thioglycolate (40%) was then carefully added to the hydrated polymer aqueous mixture, followed by potassium hydroxide. Phase B was then heated to 65° C.

Phase A was separately prepared by combining all of the ingredients and heating to 65° C. Phase A was then added to phase B using high shear mixing. The emulsion was stirred until it was homogeneous and cooled to room temperature. The pH of the resulting emulsion was then adjusted to 12.5 with the addition of a 20% solution of potassium hydroxide.

Due to the calming benefits of Boswellia extract, this cream alleviates the appearance of red dots or rashes appearing on the skin following depilation with the alkaline cream.

What is claimed is:

1. A composition suitable for treating the skin or hair comprising:
    a) at least one extract of a Boswellia plant, or at least one boswellic acid; and
    b) a carrier selected from the group consisting of branched fatty alcohols containing 8 to 32 carbon atoms, branched fatty acids containing 8 to 32 carbon atoms, unsaturated fatty alcohols containing 12 to 24 carbon atoms, unsaturated fatty acids containing 12 to 24 carbon atoms, ethoxylates of said branched fatty alcohols, ethoxylates of said branched fatty acids, ethoxylates of said unsaturated fatty alcohols, ethoxylates of said unsaturated fatty acids, esters of said alcohols, esters of said acids, ethoxylates of said esters, and mixtures thereof.

2. A composition according to claim 1, wherein the extract comprises a Boswellia Serrata gum resin.

3. A composition according to claim 1 or 2, wherein said at least one extract of a Boswellia plant comprises a mixture of boswellic acids comprising at least one of 3a-hydroxyurs-12-ene-24-oic acid, 3a-acetoxyurs-12-ene-24-oic acid, 3a-hydroxyurs-12-ene-11-keto-24-oic acid and 3a-hydroxyurs-9,12-dien-24-oic acid.

4. A composition according to claim 1 or 2, wherein the carrier is a saturated branched fatty alcohol or a saturated branched fatty acid and is liquid at room temperature.

5. A composition according to claim 4, wherein the saturated branched fatty alcohol or the saturated branched fatty acid contains from 8 to 20 carbon atoms.

6. A composition according to claim 1 or 2, wherein the carrier is an unsaturated fatty alcohol or an unsaturated fatty acid containing from 16 to 20 carbon atoms.

7. A composition according to claim 1 or 2, wherein the carrier is an ethoxylate of a branched fatty alcohol, an ethoxylate of a branched fatty acid, an ethoxylate of an unsaturated fatty alcohol or an ethoxylate of an unsaturated fatty acid.

8. A composition according to claim 7, wherein the ethoxylated derivative has from 1 to 15 ethylene oxide units per mole of fatty alcohol or per mole of fatty acid.

9. A composition according to claim 1 or 2, wherein the carrier is a branched or unsaturated fatty acid ester, esterified with a hexitol anhydride.

10. A composition according to claim 1 or 2, wherein the carrier is a monoester of glycerol and a branched fatty acid.

11. A composition according to claim 1 or 2, wherein the carrier is a monoester of propylene glycol, butylene glycol, hexylene glycol or dipropylene glycol and a branched fatty acid or an unsaturated fatty acid.

12. A composition according to claim 1 or 2, wherein the carrier is an ester of a branched fatty alcohol or an unsaturated fatty alcohol with an acid.

13. A composition according to claim 1 or 2, wherein the carrier is an ethoxylate of an ester of a hexitol anhydride and a branched fatty acid or an unsaturated fatty acid.

14. A composition according to claim 1 or 2, wherein the carrier is an ethoxylate of a monoglyceride of a branched fatty acid.

15. A composition according to claim 1, wherein the composition comprises from 0.005% to 50% by weight of at least one Boswellia extract, or at least one boswellic acid.

16. A composition according to claim 1, wherein the extract of a Boswellia plant is Boswellia Serrata gum resin extract which contains greater than 50% by weight boswellic acids.

17. A product for treating the skin or hair, comprising a composition in accordance with claim 1.

18. A method of preparing a composition suitable for treating the skin or hair comprising mixing a composition comprising:
  a) at least one extract of a Boswellia plant, or at least one boswellic acid; and
  b) a carrier selected from the group consisting of branched fatty alcohols containing 8 to 32 carbon atoms, branched fatty acids containing 8 to 32 carbon atoms, unsaturated fatty alcohols containing 12 to 24 carbon atoms, unsaturated fatty acids containing 12 to 24 carbon atoms and ethoxylates of said branched fatty alcohols, ethoxylates of said branched fatty acids, ethoxylates of said unsaturated fatty alcohols, ethoxylates of said unsaturated fatty acids, esters of said alcohols, esters of said acids, ethoxylates of said esters, and mixtures thereof with at least one cosmetically or pharmaceutically acceptable ingredient.

19. A method of treating the hair or skin which comprises applying thereto
  a) at least one member of the group consisting of an extract of a Boswellia plant and a boswellic acid; and
  b) a carrier selected from the group consisting of branched fatty alcohols containing 8 to 32 carbon atoms, branched fatty acids containing 8 to 32 carbon atoms, unsaturated fatty alcohols containing 12 to 24 carbon atoms, unsaturated fatty acids containing 12 to 24 carbon atoms and ethoxylates of said branched fatty alcohols, ethoxylates of said branched fatty acids, ethoxylates of said unsaturated fatty alcohols, ethoxylates of said unsaturated fatty acids, esters of said alcohols, esters of said acids, ethoxylates of said esters, and mixtures thereof.

20. A composition according to claim 15 wherein the composition contains from 0.05% to 25% by weight of Boswellia extract or boswellic acid.

* * * * *